United States Patent
Henkel (10) Patent No.: US 10,450,343 B2
(45) Date of Patent: Oct. 22, 2019

(54) SYNTHESIS OF CYCLIC IMIDE CONTAINING PEPTIDE PRODUCTS

(71) Applicant: SANOFI-AVENTIS DEUTSCHLAND GMBH, Frankfurt am Main (DE)

(72) Inventor: Bernd Henkel, Frankfurt am Main (DE)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 320 days.

(21) Appl. No.: 14/778,502

(22) PCT Filed: Mar. 19, 2014

(86) PCT No.: PCT/EP2014/055511
§ 371 (c)(1),
(2) Date: Sep. 18, 2015

(87) PCT Pub. No.: WO2014/147129
PCT Pub. Date: Sep. 25, 2014

(65) Prior Publication Data
US 2016/0289263 A1    Oct. 6, 2016

(30) Foreign Application Priority Data
Mar. 21, 2013   (EP) .................................. 13160380

(51) Int. Cl.
*C07K 1/107* (2006.01)
*C07K 1/00* (2006.01)
(Continued)

(52) U.S. Cl.
CPC ............ *C07K 1/1077* (2013.01); *C07K 1/006* (2013.01); *C07K 1/04* (2013.01); *C07K 1/042* (2013.01);
(Continued)

(58) Field of Classification Search
CPC ...... A61K 38/00; A61K 31/702; A61K 38/55; A61K 47/60; A61K 38/12; A61K 31/40;
(Continued)

(56) References Cited

U.S. PATENT DOCUMENTS 3,835,175 A    9/1974  Carpino et al.
3,906,031 A    9/1975  Carpino et al.
(Continued)

FOREIGN PATENT DOCUMENTS

CA    2104099    8/1993
CA    2050216    3/2003
(Continued)

OTHER PUBLICATIONS

Larsen and Holm, Journal of Peptide Research (1998) 52, 470.*
(Continued)

*Primary Examiner* — Marcela M Cordero Garcia
(74) *Attorney, Agent, or Firm* — McDonnell Boehnen Hulbert & Berghoff LLP (57) ABSTRACT

The present invention relates to a method of synthesizing a peptide product comprising at least one cyclic imide group. Further, the invention relates to a peptide product comprising at least one cyclic imide group, which is substantially free from degradation products. The peptide product may be used as a reference material for the quality control of pharmaceutical peptides, particularly for the quality control of a GLP-1 agonist like exendin peptides.

18 Claims, 3 Drawing Sheets
Specification includes a Sequence Listing.

(51) Int. Cl.
  *C07K 1/04* (2006.01)
  *C07K 14/605* (2006.01)
  *C08G 65/333* (2006.01)
  *C08G 18/38* (2006.01)

(52) U.S. Cl.
  CPC ........ *C07K 14/605* (2013.01); *C08G 18/3846* (2013.01); *C08G 65/33331* (2013.01)

(58) Field of Classification Search
  CPC .... A61K 31/675; A61K 49/0056; A61K 8/64; C07K 1/006; C07K 1/061; C07K 1/10; C07K 7/64
  See application file for complete search history.

(56) References Cited

U.S. PATENT DOCUMENTS

| | | |
|---|---|---|
| 4,108,846 A | 8/1978 | Carpino et al. |
| 4,755,591 A | 7/1988 | Koenig et al. |
| 5,169,932 A | 12/1992 | Hoeger et al. |
| 5,175,254 A | 12/1992 | Bernard et al. |
| 5,247,067 A | 9/1993 | Terukatsu et al. |
| 5,296,468 A | 3/1994 | Hoeger et al. |
| 5,352,796 A | 10/1994 | Hoeger et al. |
| 5,460,786 A | 10/1995 | Nokihara |
| 5,478,810 A | 12/1995 | Stueber et al. |
| 5,502,165 A | 3/1996 | Ho et al. |
| 5,503,805 A | 4/1996 | Sugarman et al. |
| 5,516,891 A | 5/1996 | Siwruk et al. |
| 5,536,816 A | 7/1996 | Hohler et al. |
| 5,563,032 A | 10/1996 | Fields et al. |
| 5,565,574 A | 10/1996 | Hoeger et al. |
| 5,576,296 A | 11/1996 | Bartfai et al. |
| 5,580,957 A | 12/1996 | Hoeger et al. |
| 5,602,230 A | 2/1997 | Heavner et al. |
| 5,602,231 A | 2/1997 | Cotton et al. |
| 5,607,858 A | 3/1997 | Stueber et al. |
| 5,614,608 A | 3/1997 | Krchnak et al. |
| 5,618,785 A | 4/1997 | Heavner et al. |
| 5,639,603 A | 6/1997 | Sugarman et al. |
| 5,665,975 A | 9/1997 | Sugarman et al. |
| 5,708,153 A | 1/1998 | Dower et al. |
| 5,710,123 A | 1/1998 | Heavner et al. |
| 5,710,249 A | 1/1998 | Hoeger et al. |
| 5,736,315 A | 4/1998 | Fields et al. |
| 5,744,450 A | 4/1998 | Hoeger et al. |
| 5,750,649 A | 5/1998 | Hohler et al. |
| 5,770,358 A | 6/1998 | Dower et al. |
| 5,773,575 A | 6/1998 | Ho et al. |
| 5,789,162 A | 8/1998 | Dower et al. |
| 5,830,637 A | 11/1998 | Frank et al. |
| 5,891,640 A | 4/1999 | Frank et al. |
| 5,916,876 A | 6/1999 | Heavner et al. |
| 6,022,685 A | 2/2000 | Fields et al. |
| 6,028,168 A | 2/2000 | Goodman et al. |
| 6,040,423 A | 3/2000 | Frank et al. |
| 6,056,926 A | 5/2000 | Sugarman et al. |
| 6,111,065 A | 8/2000 | Heavner et al. |
| 6,136,781 A | 10/2000 | Kitada et al. |
| 6,140,493 A | 10/2000 | Dower et al. |
| 6,143,497 A | 11/2000 | Dower et al. |
| 6,165,717 A | 12/2000 | Dower et al. |
| 6,165,730 A | 12/2000 | De Leys |
| 6,165,778 A | 12/2000 | Kedar et al. |
| 6,210,903 B1 | 4/2001 | De Leys |
| 6,268,339 B1 | 7/2001 | De Leys |
| 6,416,949 B1 | 7/2002 | Dower et al. |
| 6,469,136 B1 | 10/2002 | Bray et al. |
| 6,476,186 B1 | 11/2002 | Hsieh et al. |
| 6,492,460 B2 | 12/2002 | Haq et al. |
| 6,617,307 B1 | 9/2003 | Nishimura et al. |
| 6,649,735 B1 | 11/2003 | De Leys |
| 6,667,387 B1 | 12/2003 | De Leys |
| 6,673,769 B2 | 1/2004 | Goodman et al. |
| 6,703,480 B1 | 3/2004 | Balu |
| 6,709,828 B1 | 3/2004 | De Leys |
| 6,747,125 B1 | 6/2004 | Hoeger et al. |
| 6,767,993 B2 | 7/2004 | Bray et al. |
| 6,809,190 B2 | 10/2004 | Ikeda et al. |
| 6,849,710 B1 | 2/2005 | Arzeno |
| 7,009,037 B2 | 3/2006 | Sorensen |
| 7,049,293 B2 | 5/2006 | Nishimura et al. |
| 7,138,489 B2 | 11/2006 | Nishimura et al. |
| 7,176,282 B1 | 2/2007 | Holm et al. |
| 7,183,430 B2 | 2/2007 | Montiel et al. |
| 7,235,242 B2 | 6/2007 | Achtman et al. |
| 7,329,646 B2 | 2/2008 | Sun et al. |
| 7,348,404 B2 | 3/2008 | Holm et al. |
| 7,393,920 B2 | 7/2008 | Collins et al. |
| 7,402,663 B2 | 7/2008 | Collins et al. |
| 7,414,106 B2 | 8/2008 | Camarero et al. |
| 7,414,107 B2 | 8/2008 | Larsen et al. |
| 7,417,028 B2 | 8/2008 | Ewing et al. |
| 7,425,541 B2 | 9/2008 | Dubois et al. |
| 7,439,222 B2 | 10/2008 | Guinn et al. |
| 7,459,522 B2 | 12/2008 | Balu |
| 7,507,791 B2 | 3/2009 | Skripko |
| 7,534,763 B2 | 5/2009 | Qian et al. |
| 7,550,560 B2 | 6/2009 | Collins et al. |
| 7,563,865 B2 | 7/2009 | Collins et al. |
| 7,582,728 B2 | 9/2009 | Collins et al. |
| 7,598,222 B2 | 10/2009 | Prouty et al. |
| 7,612,168 B2 | 11/2009 | Sorensen |
| 7,691,968 B2 | 4/2010 | Evans et al. |
| 7,745,570 B2 | 6/2010 | Tomich et al. |
| 7,834,142 B2 | 11/2010 | Li |
| 7,902,488 B2 | 3/2011 | Collins et al. |
| 7,935,786 B2 | 5/2011 | Larsen |
| 7,939,628 B2 | 5/2011 | Collins et al. |
| 7,960,349 B2 | 6/2011 | Ewing et al. |
| 7,960,506 B2 | 6/2011 | Nash |
| 7,981,998 B2 | 7/2011 | Nash |
| 8,034,787 B2 | 10/2011 | Dubois |
| 8,058,393 B2 | 11/2011 | Collins et al. |
| 8,058,394 B2 | 11/2011 | Kajihara et al. |
| 8,097,586 B2 | 1/2012 | Lv et al. |
| 8,114,959 B2 | 2/2012 | Juul-Mortensen |
| 8,153,761 B2 | 4/2012 | Collins et al. |
| 8,178,474 B1 | 5/2012 | Melnyk et al. |
| 8,202,837 B2 | 6/2012 | Bush et al. |
| 8,227,571 B2 | 7/2012 | Chen et al. |
| 8,252,896 B2 | 8/2012 | Hsiao et al. |
| 8,426,560 B2 | 4/2013 | Collins et al. |
| 8,435,800 B2 | 5/2013 | Gengrinovitch |
| 8,609,809 B2 | 12/2013 | Nash |
| 8,620,595 B2 | 12/2013 | Krokhin et al. |
| 8,710,011 B2 | 4/2014 | Garcia et al. |
| 8,716,221 B2 | 5/2014 | Lv et al. |
| 8,802,819 B2 | 8/2014 | Fernando et al. |
| 8,846,862 B2 | 9/2014 | Collins et al. |
| 8,933,196 B2 | 1/2015 | Chen et al. |
| 8,946,166 B2 | 2/2015 | Garcia et al. |
| 8,993,716 B2 | 3/2015 | Carreno et al. |
| 9,175,056 B2 | 11/2015 | Nash |
| 9,206,223 B2 | 12/2015 | Nash et al. |
| 9,211,522 B2 | 12/2015 | Collins et al. |
| 9,260,474 B2 | 2/2016 | Pan et al. |
| 9,263,194 B2 | 2/2016 | Seo et al. |
| 9,266,921 B2 | 2/2016 | Garcia et al. |
| 9,290,537 B2 | 3/2016 | Madded et al. |
| 9,314,521 B2 | 4/2016 | Ossendorp et al. |
| 9,315,564 B2 | 4/2016 | Serraima et al. |
| 9,364,772 B2 | 6/2016 | Larsen et al. |
| 9,393,186 B2 | 7/2016 | Alminana et al. |
| 9,394,336 B2 | 7/2016 | Nash et al. |
| 9,394,341 B2 | 7/2016 | Wen et al. |
| 9,422,330 B2 | 8/2016 | Wu et al. |
| 9,605,344 B2 | 3/2017 | Jiang et al. |
| 9,724,622 B2 | 8/2017 | Anwer |
| 9,766,217 B2 | 9/2017 | Kidal et al. |
| 2002/0058788 A1 | 5/2002 | Sheppeck |
| 2003/0191049 A1 | 10/2003 | Amblard |
| 2004/0086949 A1* | 5/2004 | Holm .............. A61K 39/04 435/7.1 |

(56) References Cited

U.S. PATENT DOCUMENTS

| | | | |
|---|---|---|---|
| 2004/0235049 A1 | 11/2004 | Melnyk et al. | |
| 2006/0079667 A1 | 4/2006 | Skripko | |
| 2006/0167224 A1 | 7/2006 | Tonosaki et al. | |
| 2007/0129537 A1 | 6/2007 | Camarero et al. | |
| 2009/0111152 A1* | 4/2009 | Sherman | C12P 17/14 435/120 |
| 2009/0197315 A1* | 8/2009 | Barron | A61K 31/185 435/183 |
| 2010/0021510 A1 | 1/2010 | Carreno et al. | |
| 2010/0056755 A1 | 3/2010 | Hsiao et al. | |
| 2010/0292436 A1 | 11/2010 | Bai et al. | |
| 2011/0245461 A1 | 10/2011 | Krokhin et al. | |
| 2011/0313131 A1 | 12/2011 | Christelle et al. | |
| 2011/0319594 A1 | 12/2011 | Bai et al. | |
| 2012/0296068 A1 | 11/2012 | Chen et al. | |
| 2013/0289241 A1 | 10/2013 | Bai et al. | |
| 2014/0187745 A1 | 7/2014 | Wen et al. | |
| 2015/0051372 A1 | 2/2015 | Qin et al. | |
| 2015/0073122 A1 | 3/2015 | Seo et al. | |
| 2015/0232527 A1 | 8/2015 | Gong et al. | |
| 2015/0274799 A1 | 10/2015 | Gong et al. | |

FOREIGN PATENT DOCUMENTS

| | | | |
|---|---|---|---|
| CA | 2765196 | 12/2004 | |
| CA | 2458084 | 9/2005 | |
| CA | 2915484 | 6/2016 | |
| CN | 1699404 | 11/2005 | |
| CN | 101255191 | 9/2008 | |
| CN | 101357937 | 2/2009 | |
| CN | 101357938 | 2/2009 | |
| CN | 101463078 | 6/2009 | |
| CN | 101463081 | 6/2009 | |
| CN | 101525368 | 9/2009 | |
| CN | 101525370 | 9/2009 | |
| CN | 101538324 | 9/2009 | |
| CN | 102174082 | 9/2011 | |
| CN | 102558338 | 7/2012 | |
| CN | 102875663 | 1/2013 | |
| CN | 103242443 | 8/2013 | |
| CN | 103333237 | 10/2013 | |
| CN | 103536912 | 1/2014 | |
| CN | 103613655 | 3/2014 | |
| CN | 103965285 | 8/2014 | |
| CN | 104086631 | 10/2014 | |
| CN | 102411801 | 12/2014 | |
| CN | 105111303 | 12/2015 | |
| CN | 105585612 | 5/2016 | |
| DE | 4244565 | 7/1994 | |
| DE | 4341471 | 6/1995 | |
| DE | 19543628 | 5/1997 | |
| EP | 0402313 | 12/1990 | |
| EP | 0445801 | 9/1991 | |
| EP | 0450715 | 10/1991 | |
| EP | 1445260 | 8/2004 | |
| EP | 1923397 | 5/2008 | |
| FI | 20065208 | 3/2006 | |
| FR | 2864830 | 7/2005 | |
| GB | 200105069 | 4/2001 | |
| GB | 200210185 | 6/2002 | |
| GB | 200613147 | 8/2006 | |
| WO | WO 91/06543 | 5/1991 | |
| WO | WO 92/17025 | 10/1992 | |
| WO | WO 92/20709 | 11/1992 | |
| WO | WO 93/03056 | 2/1993 | |
| WO | WO 93/06121 | 4/1993 | |
| WO | WO 93/18054 | 9/1993 | |
| WO | WO 93/24526 | 12/1993 | |
| WO | WO 93/25571 | 12/1993 | |
| WO | WO 94/04568 | 3/1994 | |
| WO | WO 94/05314 | 3/1994 | |
| WO | WO 94/09032 | 4/1994 | |
| WO | WO 94/14836 | 7/1994 | |
| WO | WO 95/00474 | 1/1995 | |
| WO | WO 95/08561 | 3/1995 | |
| WO | WO 95/12608 | 5/1995 | |
| WO | WO 95/14787 | 6/1995 | |
| WO | WO 95/21858 | 8/1995 | |
| WO | WO 95/27727 | 10/1995 | |
| WO | WO 96/22157 | 7/1996 | |
| WO | WO 96/34012 | 10/1996 | |
| WO | WO 96/40759 | 12/1996 | |
| WO | WO 97/11372 | 3/1997 | |
| WO | WO 98/11125 | 3/1998 | |
| WO | WO 98/11126 | 3/1998 | |
| WO | WO 98/31791 | 7/1998 | |
| WO | WO 99/46283 | 9/1999 | |
| WO | WO 00/33888 | 6/2000 | |
| WO | WO 01/34635 | 5/2001 | |
| WO | WO 01/38342 | 5/2001 | |
| WO | WO 01/55213 | 8/2001 | |
| WO | WO 01/95945 | 12/2001 | |
| WO | WO 02/20554 | 3/2002 | |
| WO | WO 02/40512 | 5/2002 | |
| WO | WO 02/053606 | 7/2002 | |
| WO | WO 02/070546 | 9/2002 | |
| WO | WO 02/074782 | 9/2002 | |
| WO | WO 02/083606 | 10/2002 | |
| WO | WO 03/018605 | 3/2003 | |
| WO | WO 03/093301 | 11/2003 | |
| WO | WO 03/093302 | 11/2003 | |
| WO | WO 03/095475 | 11/2003 | |
| WO | WO 2004/018502 | 3/2004 | |
| WO | WO 2004/022578 | 3/2004 | |
| WO | 2004/035623 A2 | 4/2004 | |
| WO | WO 2004/035623 * | 4/2004 | C07K 14/575 |
| WO | WO 2004/089504 | 10/2004 | |
| WO | WO 2004/105685 | 12/2004 | |
| WO | WO 2004/105790 | 12/2004 | |
| WO | WO 2005/019262 | 3/2005 | |
| WO | WO 2005/063791 | 7/2005 | |
| WO | WO 2005/080424 | 9/2005 | |
| WO | WO 2005/087794 | 9/2005 | |
| WO | WO 2006/008050 | 1/2006 | |
| WO | WO 2006/014287 | 2/2006 | |
| WO | WO 2006/040037 | 4/2006 | |
| WO | WO 2006/054310 | 5/2006 | |
| WO | WO 2006/108594 | 10/2006 | |
| WO | WO 2006/117227 | 11/2006 | |
| WO | WO 2006/127048 | 11/2006 | |
| WO | WO 2006/127948 | 11/2006 | |
| WO | WO 2007/033383 | 3/2007 | |
| WO | WO 2007/056681 | 5/2007 | |
| WO | WO 2007/065691 | 6/2007 | |
| WO | WO 2007/113356 | 10/2007 | |
| WO | WO 2007/113386 | 10/2007 | |
| WO | WO 2007/139589 | 12/2007 | |
| WO | WO 2007/140284 | 12/2007 | |
| WO | WO 2008/001109 | 1/2008 | |
| WO | WO 2008/028974 | 3/2008 | |
| WO | WO 2008/044890 | 4/2008 | |
| WO | 2008/071972 A1 | 6/2008 | |
| WO | WO 2008/076904 | 6/2008 | |
| WO | 2008/101017 A2 | 8/2008 | |
| WO | WO 2008/109079 | 9/2008 | |
| WO | WO 2008/137165 | 11/2008 | |
| WO | 2008/152403 A1 | 12/2008 | |
| WO | WO 2009/003666 | 1/2009 | |
| WO | WO 2009/074483 | 6/2009 | |
| WO | WO 2009/098707 | 8/2009 | |
| WO | WO 2009/106343 | 9/2009 | |
| WO | WO 2009/132231 | 10/2009 | |
| WO | WO 2009/138488 | 11/2009 | |
| WO | 2009/155258 A2 | 12/2009 | |
| WO | 2010/011439 A2 | 1/2010 | |
| WO | WO 2010/009872 | 1/2010 | |
| WO | WO 2010/028122 | 3/2010 | |
| WO | WO 2010/028131 | 3/2010 | |
| WO | WO 2010/033254 | 3/2010 | |
| WO | WO 2010/034032 | 3/2010 | |
| WO | WO 2011/107447 | 3/2010 | |
| WO | 2010/070251 A1 | 6/2010 | |
| WO | 2010/070252 A1 | 6/2010 | |

(56) References Cited

FOREIGN PATENT DOCUMENTS

| WO | 2010/070253 A1 | 6/2010 |
|---|---|---|
| WO | 2010/070255 A1 | 6/2010 |
| WO | WO 2010/063122 | 6/2010 |
| WO | WO 2010/063123 | 6/2010 |
| WO | WO 2010/063124 | 6/2010 |
| WO | 2010/096052 A1 | 8/2010 |
| WO | 2010/096142 A1 | 8/2010 |
| WO | WO 2010/091893 | 8/2010 |
| WO | WO 2010/118880 | 10/2010 |
| WO | 2010/148089 A1 | 12/2010 |
| WO | 2011/006497 A1 | 1/2011 |
| WO | WO 2011/009626 | 1/2011 |
| WO | WO 2011/047868 | 4/2011 |
| WO | 2011/075393 A2 | 6/2011 |
| WO | 2011/094337 A1 | 8/2011 |
| WO | 2011/117416 A1 | 9/2011 |
| WO | 2011/119657 A1 | 9/2011 |
| WO | 2011/117415 A1 | 12/2011 |
| WO | 2011/160630 A2 | 12/2011 |
| WO | WO 2011/161007 | 12/2011 |
| WO | WO 2012/055509 | 5/2012 |
| WO | WO 2012/057624 | 5/2012 |
| WO | 2012/088116 A2 | 6/2012 |
| WO | WO 2012/085279 | 6/2012 |
| WO | 2012/138941 A1 | 10/2012 |
| WO | WO 2012/130775 | 10/2012 |
| WO | WO 2012/155780 | 11/2012 |
| WO | WO 2012/161654 | 11/2012 |
| WO | WO 2013/051936 | 4/2013 |
| WO | WO 2013/093639 | 6/2013 |
| WO | WO 2013/156493 | 10/2013 |
| WO | WO 2013/170963 | 11/2013 |
| WO | WO 2014/118797 | 8/2014 |
| WO | WO 2015/009701 | 1/2015 |
| WO | WO 2015/038919 | 3/2015 |
| WO | WO 2015/078477 | 6/2015 |
| WO | WO 2015/128687 | 9/2015 |
| WO | WO 2016/020349 | 2/2016 |
| WO | WO 2016/057683 | 4/2016 |
| WO | WO 2016/067271 | 5/2016 |
| WO | WO 2016/084100 | 6/2016 |
| WO | WO 2017/162653 | 9/2017 |

OTHER PUBLICATIONS

Louis A. Carpino. The 9-Fluorenylmethyloxycarbonyl Family of Base-Sensitive Amino-Protecting Groups. Acc. Chem. Res. 1987, 20, 401-407. (Year: 1987).*

Fields et al. Solid phase peptide synthesis utilizing 9-fluorenylmethoxycarbonyl amino acids. Int J Pept Protein Res. Mar. 1990;35(3):161-214. (Year: 1990).*

Anonymous: Lixisenatide—Wikipedia, the free encyclopedia, Feb. 24, 2013, pp. 1-4, XP055120784, Retrieved from internet: URL: http://en.wikipedia.org/w/index. php?title= Lixisenatide&olidid= 540119995 (retrieved on May 28, 2014).

Alvarez-Gutierrez et al., "Solid phase synthesis of 1,3-disubstituted succinimides", Tetrahedron Letters, 41(5): 609-612 (2000).

Aswad et al., "Isoaspartate in peptides and proteins: formation, significance, and analysis", Journal of Pharmaceutical and Biomedical Analysis, 21: 1129-1136 (2000).

Cebrian et al., "Synthesis of peptide sequences related to thrombospondin: factors affecting aspartimide by-product formation", J. Peptide Res., 62: 238-244 (2003).

Day et al., "A new glucagon and GLP-1 co-agonist eliminates obesity in rodents", Nature Chemical Biology, 5(10): 749-57 (2009).

De Boni et al., "Analysis of asparyl peptide degradation products by high-performance liquid chromatography and high-performance liquid chromatography-mass spectrometry", Journal of Chromatography A, 1022: 95-102 (2004).

El-Faham et al., "Peptide coupling reagents, more than a letter soup", Chem. Rev., 111: 6557-6602 (2011).

Flaih et al., "A one-step synthesis of aminosuccinyl peptides", Synlett, 6: 896-898 (2000).

Geiger et al., "Deamidation, isomerization, and racemization at asparaginyl and aspartyl residue in peptides", Journal of Biological Chemistry, 262(2): 785-794 (1987).

Hekman et al., "Isolation and identification of cyclic imide and deamidation products in heat stressed pramlinitide injection drug product", Journal of Pharmaceutical and Biomedical Analysis, 20: 763-772 (1999).

Hjorth et al., "Glucagon and glucagon-like peptide 1: Selective receptor recognition via distinct peptides epitopes", The Journal of Biological Chemistry, 269(48): 30121-30124 (1994).

Houchin et al., "Deamidation, acylation and proteolysis of a model peptide in PLGA films", Journal of Controlled Release, 112: 111-119 (2006).

King et al., "A cleavage method which minimizes side reactions following Fmoc solid phase peptide synthesis", Int. Peptide Protein Res., 36: 255-266 (1990).

Linder et al., "Age-dependent deamidation of asparagine residues in proteins", Experimental Gerontology, 36: 1551-1563 (2001).

Mergler et al., "The aspartimide problem in Fmoc-based SSPS. Part II", Journal of Peptide Science, 9: 36-46 (2003).

Mergler et al., "The aspartimide problem in Fmoc-based SSPS. Part II", Journal of Peptide Science, 9: 518-526 (2003).

Mergler et al., "The aspartimide problem in Fmoc-based SSPS. Part III", Journal of Peptide Science, 11: 650-657 (2005).

Ritz-Timme et al., "Racemization of aspartic acid in human proteins", Ageing Research Reviews, 12: 43-59 (2002).

Subiros-Funosas et al., "Aspartimide formation in peptide chemistry: occurrence, prevention strategies and the role of hydroxylamines", Tetrahedron, 67(45): 8595-8606 (2011).

Vintner at al., "Synthesis of stereoisomers and isoforms of a tryptic heptapeptide fragment of human growth hormone and analysis by reverse-phase HPLC and capillary electrophoresis", European Journal of Biochemistry, 235 (1-2): 304-309 (1996).

Extended European Search Report issued in European Application No. 13160380.5 (dated Jul. 9, 2013).

International Search Report and Written Opinion issued in International Patent Application No. PCT/EP2014/055511 (dated Jun. 17, 2014).

International Preliminary Report on Patentability (Chapter II) issued in International Patent Application No. PCT/EP2014/055511 (dated Apr. 13, 2015).

* cited by examiner

Figure 1

-Asn(28)-Gly(29)- in AVE0010

Aspartimide

-Asp(9)-Leu(10)- in AVE0010

Aspartimide

SEQUENCE LISTING

```
<160> NUMBER OF SEQ ID NOS: 1

<210> SEQ ID NO 1
<211> LENGTH: 44
<212> TYPE: PRT
<213> ORGANISM: Artificial Sequence
<220> FEATURE:
<223> OTHER INFORMATION: Lixisenatide GLP-1 agonist

<400> SEQUENCE: 1

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Lys Lys Lys Lys Lys Lys
        35                  40
```

SYNTHESIS OF CYCLIC IMIDE CONTAINING PEPTIDE PRODUCTS

CROSS-REFERENCE TO RELATED APPLICATIONS

This application is a national stage application under 35 U.S.C. § 371 of International Application No. PCT/EP2014/055511, filed Mar. 19, 2014, which claims priority to the European Patent Application No. 13160380.5, filed on Mar. 21, 2013.

SUMMARY OF DISCLOSURE

The present invention relates to a method of synthesizing a peptide product comprising at least one cyclic imide group. Further, the invention relates to a peptide product comprising at least one cyclic imide group, which is substantially free from degradation products. The peptide product may be used as a reference material for the quality control of pharmaceutical peptides, particularly for the quality control of GLP-1 agonists like exendin peptides.

Using well-known recombinant DNA and chemical solid phase synthesis processes, several proteins and peptides have been synthesized for pharmaceutical use. The production of these proteins and peptides, however, often leads to a multiplicity of undesired synthesis by-products. This is especially the case when they are produced by solid phase synthesis. With an increase in length of the peptide/protein, leading to an increase in the synthesis steps, these by-products may be present in 50 to 70% of the crude product.

The by-products may include peptide products containing cyclic imide groups, e.g. aspartimides or glutarimides. Such cyclic imide groups are generated during or after the solid phase synthesis, e.g. when removing a peptide from the solid phase carrier or when formulating or storing a peptide composition (Geiger & Clarke, J. Biol. Chem. 262 (1987), 785-794; Hekman et al., J Pharm. Biomed. Anal. 20 (1999), 763-772; Lindner & Helliger, Exp. Gerontol. 36 (2001), 1551-1563; Aswad et al., J. Pharm. Biomed. Anal. 21 (2000), 1129-1136; Ritz-Timme & Collins, Ageing Res. Rev. 1 (2002), 43-59; Mergler et al., J. Pept. Sci. 9 (2003), 36-46; Mergler et al., J. Pept. Sci. 9 (2003), 518-526: Mergler et al., J. Pept. Sci. 11 (2005), 650-657; Cebrian et al., J. Pept. Res. 62 (2003), 238-244; De Boni et al., J. Chrom. A. 1022 (2004), 95-102; and Houchin et al., J. Contr. Release 112 (2006), 111-119).

A targeted synthesis of peptide products containing cyclic imide groups is not known. In the past, aspartimides or glutarimides have been generated by "forced degradation" procedures, wherein a peptide comprising the amino acids Asp or Asn is subjected to degradation conditions, e.g. stirring at pH 4 or pH 8 for one to two days, optionally at an elevated temperature of about 40 to about 50° C. These methods, however, have the disadvantage that in addition to the desired products, numerous other degradation products are obtained. Particularly, the cyclic imide group may be subject to further reactions, e.g. racemisation, formation of an isoaspartate peptide, conversion from Asn to Asp, opening of the aspartimide by nucleophilic reagents, peptide bond cleavage, etc. Thus, after performing a forced degradation, it is often difficult to purify the desired cyclic imide product from a complex mixture of peptidic compounds.

In order to overcome these difficulties occurring in the manufacture and purification of the cyclic imide peptide products, the present inventors have developed a targeted synthesis for cyclic imide containing peptides.

This method is shown exemplarily for the peptide Lixisenatide (AVE0010), a GLP-1 agonist having a length of 44 amino acids long. The amino acid sequence of Lixisenatide is shown in SEQ ID NO:1:

H-G-E-G-T-F-T-S-D-L-S-K-Q-M-E-E-E-A-V-R-L-F-I-E-

W-L-K-N-G-G-P-S-S-G-A-P-P-S-K-K-K-K-K-K-NH$_2$

Lixisenatide is produced by a chemical solid phase synthesis process.

Figure 1:
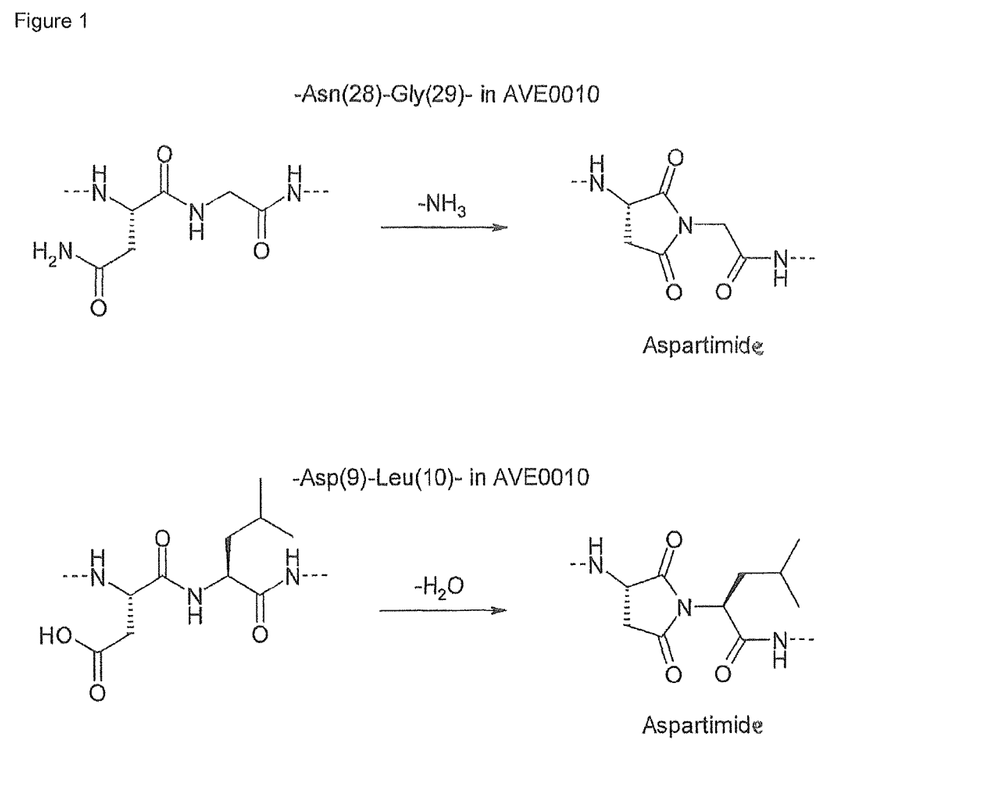
FIG. 1 illustrates the formation of aspartimides in AVE0010, namely on position-Asn(28)-Gly(29)- and Asp(9)-Leu(10).

Aspartimides may be formed from peptide sequences -Asn-X- or -Asp-X-, wherein X denotes a C-terminally adjacent amino acid residue. In the former case, the cyclisation involves removal of ammonia (NH$_3$) and in the latter case, removal of water (H$_2$O). In FIG. 1, the formation of aspartimides in AVE0010, namely on position -Asn(28)-Gly(29)- and Asp(9)-Leu(10) is illustrated. The resulting products are designated [Asp(9)-H$_2$O]-AVE0010 and [Asn(28)-NH$_3$]-AVE0010, respectively. In principle, the same reaction results in the formation of glutarimides from the amino acids Gln or Glu.

The present inventors have now found that a targeted synthesis of cyclic imide groups is possible when using an amino acid building block with an unprotected COOH or CONH$_2$ side chain, e.g. Asp, Asn or Glu, Gln in the coupling step during peptide synthesis at predetermined positions where formation of cyclic imide groups is desired. At other positions where formation of cyclic imide groups is not desired, amino acid building blocks with a protected COOH or CONH$_2$ side chain may be used in the synthesis. By increasing the coupling time and repeated addition of coupling reagents, the cyclic imide groups may be obtained in nearly quantitative yield. Thus, the present invention allows selective formation of cyclic imide groups at predetermined positions of a peptide sequence without affecting other positions of the peptide sequence potentially susceptible to cyclic imide group formation.

Figure 2:
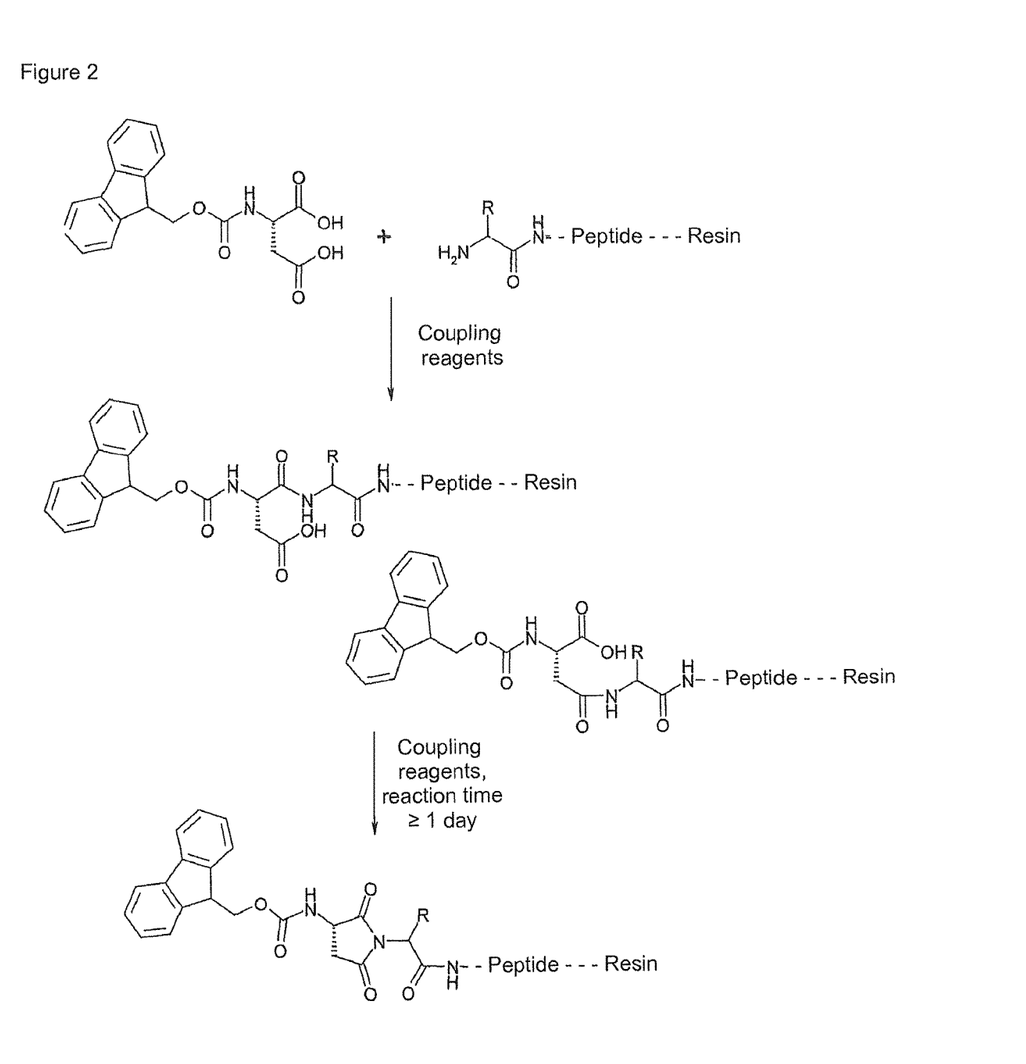
FIG. 2 illustrates the formation of an aspartimide group.

In FIG. 2, formation of an aspartimide group is shown. An amino-protected (e.g. by Fmoc) protected Asp building block with an unprotected carboxy side chain is added to a carrier resin-bound peptide derivative with a free amino group in the presence of coupling reagents. Formation of the aspartimide group is favoured by increasing the coupling time to ≥1 day and repeated adding of coupling reagents. The other steps of peptide synthesis, i.e. previous and/or subsequent steps, may be carried out under standard conditions. It should be avoided, however, to use piperidine for the cleavage of the Fmoc protection group, because this may lead to an opening of the aspartimide ring.

The method of the present invention allows a targeted synthesis of cyclic imide peptide products in high yield and purity. These peptide products may e.g. be used as reference materials for the quality control of pharmaceutical peptide products such as lixisenatide.

A subject-matter of the present invention is a method of synthesizing a peptide product comprising at least one cyclic imide group of formula (I) or a salt or solvate thereof:

wherein
R₁ is a bridge (or biradical) of one or two atoms lengths,
R₂ is an amino acid side chain,
* denotes an asymmetric C atom, preferably in the L-configuration, and
(*) denotes an optionally asymmetric C atom, preferably in the L-configuration,
comprising the steps:
(a) coupling a synthesis building block of formula (II):

wherein
X is an amino protecting group,
Y is an unprotected carboxy or carboxamido group,
Z is a carboxy group, and
* denotes an asymmetric C atom, preferably in the L-configuration, to a peptide product of formula (III)

wherein
$R_{2'}$ is an optionally protected amino acid side chain,
$R_3$ is a peptidic residue, preferably bound to a solid phase carrier, and
(*) denotes an optionally asymmetric C atom, preferably in the L-configuration, under conditions wherein the cyclic imide group of formula (I) is formed,
(b) cleaving off the amino protecting group X,
(c) optionally continuing the peptide synthesis, and
(d) optionally purifying the peptide product (I).

A further subject-matter of the present invention is a peptide product comprising at least one cyclic imide group of formula (I) or a salt or solvate thereof:

wherein
R₁ is a bridge (or biradical) of one or two atoms lengths,
R₂ is an amino acid side chain,
* denotes an asymmetric C atom, and
(*) denotes an optionally asymmetric C atom.

Particularly the peptide product is a GLP-1 agonist such as an exendin peptide, more particularly lixisenatide (AVE0010).

A further subject-matter of the present invention is the use of a peptide product of formula (I) or a salt or solvate thereof as described above as a reference material for the quality control of pharmaceutical peptides, particularly of GLP-1 agonist peptides such as exendin peptides, e.g. lixisenatide.

Still, a further subject-matter of the invention is a reagent kit for determining the amount of impurities in a lixisenatide (AVE0010) product composition comprising:
(i) at least one stock preparation of [Asp(9)-H₂O]-AVE0010 and/or
(ii) at least one stock preparation of [Asn(28)-NH₃]-AVE0010.

Still, a further subject-matter of the present invention is a method for the quality control of a composition comprising a pharmaceutical peptide product, particularly a GLP-1 agonist peptide product, e.g. an exendin peptide product, more particularly a lixisenatide (AVE0010) product, comprising quantitatively determining the amount of a peptide product with a cyclic imide group of formula (I) or a salt or solvate thereof in said composition.

DETAILED DESCRIPTION OF THE DISCLOSURE

The present invention relates to a method of synthesizing a peptide product. The term "peptide product" encompasses peptides and proteins having a length of at least 5 or at least 10 amino acids and up to 50 or up to 100 amino acids or even longer. The peptide product may consist of genetically encoded amino acid building blocks or may comprise non-genetically encoded amino acid building blocks, e.g. non-naturally occurring amino acids, D-amino acids or chemically modified amino acids or may consist of several peptide chains linked e.g. by disulfide bridges. The peptide product may further contain modifications at the N- and/or C-terminus and/or at side chains, e.g. an acylation, an amidation or the addition of non-peptide side chain groups such as lipophilic groups. The peptide product may be linear or circular. Preferably, the peptide product has a length from 5-100 amino acids.

The peptide product of the invention may be in the form of a salt, e.g. a pharmaceutically acceptable salt or solvate, e.g. a hydrate. Examples of pharmaceutically acceptable salts are described in Remington: The Science and Practice of Pharmacy, (20ᵗʰ ed.) ed. A. R. Gennaro A. R., 2000, Lippencott Williams & Wilkins or in Handbook of Pharmaceutical Salts, Properties, Selection and Use, e.d. P. H. Stahl, C. G. Wermuth, 2002, jointly published by Verlag Helvetica Chimic Acta, Zurich, Switzerland, and Wiley-VCH, Weinheim, Germany. Preferably, the salt is a trifluoroacetate or acetate salt.

The peptide product comprises at least one amino acid residue capable of forming a cyclic imide group of formula (I), particularly an amino acid residue having a side chain with a carboxy or carboxamide group such as Asp, Asn, Glu or Gln, located N-terminally to an amino acid residue with an N-atom in the peptide chain accessible for cyclisation. The C-terminally located amino acid residue may e.g. be selected from Gly, Leu, His, Asp, Arg, Phe, Ala, Cys, Gln, Glu, Lys, Met, Asn, Ser, Tyr, Thr, Ile, Trp in their D- or L-configuration and unnatural (e.g. non-genetically encoded) amino acids, which are e.g. listed in supplier's catalogues.

Preferably, the peptide product which has been synthesized according to the present invention comprises at least one cyclic imide group of formula (I) and at least one amino acid residue having a side chain with a carboxy or carboxamide group such as Asp, Asn, Glu or Gln, which is not present as cyclic imide group.

The synthesis of the peptide product is carried out by chemical synthesis procedures, particularly by a solid phase synthesis procedure which is well-known in the art, e.g. a procedure involving a stepwise coupling of synthesis building blocks to a peptide chain bound to a carrier, e.g. a synthetic resin. In a preferred embodiment of the invention, the peptide product is a GLP-1 agonist peptide, such as an an exendin peptide, e.g. exendin-4, liraglutide or lixisenatide (AVE0010) or GLP-1 receptor agonist like GLP-1 or -2, oxyntomodulin, glucagon or peptides which bind and activate both the glucagon and the GLP-1 receptor (Hjort et al., Journal of Biological Chemistry, 269, 30121-30124, 1994; Day J W et al., Nature Chem. Biol. 5:749-757, 2009) and suppress body weight gain and reduce food intake which are described in patent applications WO 2008/071972, WO 2008/101017, WO 2009/155258, WO 2010/096052, WO 2010/096142, WO 2011/075393, WO 2008/152403, WO 2010/070251, WO 2010/070252, WO 2010/070253, WO 2010/070255, WO 2011/160630, WO 2011/006497, WO 2011/152181, WO 2011/152182, WO 2011/117415, WO 2011/117416, the contents of which are herein incorporated by reference, or GIP and peptides which bind and activate both the GIP and the GLP-1 receptor and optionally the glucagon receptor, and improve glycemic control, suppress body weight gain and reduce food intake as described in patent applications WO 2011/119657, WO 2012/138941, WO 2010/011439, WO 2010/148089, WO 2011/094337, and WO 2012/088116, the contents of which are herein incorporated by reference. Further examples of peptide products are insulins and insulin analogues or DPP-4 inhibitors. More preferably, the peptide product is an exendin peptide, most preferably lixisenatide (AVE0010).

Step (a) of the method of the invention comprises coupling a synthesis acid building block of formula (II) to a peptide product of formula (III). The building block (II) comprises a group Z, wherein Z is a carboxy group capable of coupling to an amino group under coupling conditions, i.e. in the presence of coupling reagents in an organic solvent. Further, the amino acid building block (II) comprises a side chain $R_1Y$, wherein $R_1$ is a biradical or bridge having a length of one to two atoms, preferably a $C_1$-$C_2$ group, more preferably a —$CH_2$— or a —$CH_2$—$CH_2$— group. Y is an unprotected carboxy or carboxamido group. Building block (II) also has a protected amino group NHX, wherein X is an amino protecting group, e.g. a fluorenylmethoxycarbonyl (Fmoc) group or another base-labile protecting group or an acid-labile protecting group such as butoxycarbonyl (Boc), trityl (Trt) or a protecting group selected from carboxybenzyl (Cbz), allyloxycarbonyl (Alloc) or another protecting group for amino groups mentioned in Green's Protective Groups in Organic Synthesis, John Wiley & Sons, 4th ed. 2006, chapter 7, Protection for the Amino Group, mentioned in Protecting Groups, P. J. Kocierski, Thieme, $3^{rd}$ ed. 2005, chapter 8, Amino Protecting Groups or mentioned in Houben-Weyl, Methods in Organic Chemistry, Synthesis of Peptides and Peptidomimetics, $4^{th}$ ed. 2001, chapter 2, Protection of Functional groups, the contents of which are herein incorporated by references.

Building block (II) further has an asymmetric carbon atom denoted by *. Preferably, the asymmetric carbon atom is in the L-configuration.

Peptide product (III), which may be an intermediate product of peptide synthesis, has a free amino group capable of reacting with group Z of synthesis building block (II) under coupling conditions, i.e. in the presence of coupling reagents in an organic solvent. The intermediate peptide product comprises an N-terminal amino acid building block with an optionally protected amino acid side chain $R_{2'}$ and a peptidic residue $R_3$ constituted of one or more amino acids. The peptidic residue is preferably bound to a solid phase carrier, e.g. a resin suitable for peptide synthesis. Peptide product (III) may also contain an asymmetric carbon atom denoted as (*) when $R_{2'}$ is different from H. Preferably, the asymmetric carbon atom is in the L-configuration.

The coupling conditions in step (a) preferably comprise a reaction time of at least 4 h, 8 h, 12 h, 16 h or 24 h and up to 48 h, 72 h or 96 h. Further, the coupling conditions preferably comprise a reaction temperature between 0 and 50° C., preferably between 15 and 40° C. The coupling reaction is carried out in the presence of a coupling reagent such as TBTU (O-(benzotriazol-1-yl)-N,N,N',N'-tetramethyluronium tetrafluoroborate, HBTU (2-(1H-benzotriazole-1-yl),1,1,3,3-tetramethyluronium) hexafluorophosphate or HOBt (1-hydroxybenzotriazole)/DIC (diisopropylcarbodiimide) and an organic base such as DIPEA (diisopropylethylamine) in a suitable organic solvent such as DMF (dimethylformamide), or other coupling reagents. For example, coupling reagents named in A. El-Faham, F. Albericio, Chem. Rev. 2011, 111, 6557-6602, can be employed, the content of which is herein incorporated.

Preferably, the coupling step is carried out under conditions wherein the yield of the cyclic imide product is ≥50%, ≥60%, ≥70%, ≥80% or ≥90% based on the amount of the total yield in coupling step (a), i.e. the amount of amino acid building block (II) coupled to the peptide intermediate product (III).

Step (b) of the inventive method comprises cleaving off the amino protecting group X after the coupling step in the presence of a deprotecting agent such as DBU (1,8-diazabicyclo[5.4.0]undec-7-ene). Further suitable deprotecting agents are mentioned in Green's Protective Groups in Organic Synthesis, John Wiley & Sons, $4^{th}$ ed. 2006, chapter 7, Protection for the Amino Group, mentioned in Protecting Groups, P. J. Kocierski, Thieme, $3^{rd}$ ed. 2005, chapter 8, Amino Protecting Groups or mentioned in Houben-Weyl, Methods in Organic Chemistry, Synthesis of Peptides and Peptidomimetics, $4^{th}$ ed. 2001, chapter 2, Protection of Functional groups, the contents of which are herein incorporated by references. The use of piperidine as a deprotecting agent is less recommended since it results in a ring opening of the cyclic imide group.

Optional Step (c) comprises continuing the synthesis of the peptide product after formation of the cyclic imide group. The synthesis may be continued under standard conditions except that the use of piperidine, as a deprotecting reagent should be avoided. Step (c) may also comprise deprotecting side chain protected amino acid groups and cleaving the peptide off from the solid phase carrier. These procedures may be carried out under standard conditions as known in the art.

Optional step (d) comprises purifying the peptide product (I) from other peptides obtained in the peptide synthesis procedure. Preferably, the purification involves a chromatographic procedure. The term "chromatographic procedure" involves a chromatographic procedure suitably for the purification of peptide products, including e.g. ion exchange chromatography, hydrophobic interaction chromatography, affinity chromatography, size exclusion chromatography, and particularly high performance liquid chromatography (HPLC) and more particularly Reverse Phase HPLC, or combinations of several procedures. More preferably, the chromatographic procedure involves at least one Reverse Phase HPLC chromatography step.

As a result of the inventive synthesis method, an isolated and purified peptide product comprising a cyclic imide group of formula (I) may be obtained. Preferably, this peptide product is substantially free from degradation products, e.g. deamidation products, racemised products and/or isoasparagine-containing products. Preferably, the amount of degradation products is less than 1%, 0.5% or 0.1% based on the amount of the total product as measured by means of chromatoghraphy, e.g. HPLC.

The peptide product comprises at least one cyclic imide group, e.g. 1, 2 or 3 cyclic imide groups. Preferably, the peptide product comprises one or two cyclic imide groups. More preferably, the peptide product comprises one or more uncyclisized cyclic imide groups.

The peptide product is preferably a therapeutic peptide, e.g. an exendin peptide, particularly lixisenatide (AVE0010) having at least one cyclic imide group. Specific examples of preferred peptide products are [Asp(9)-H$_2$O]-AVE0010, [Asn(28)-NH$_3$]-AVE0010, [Asp(9)-H$_2$O]-Exendin-4, [Asn(28)-NH$_3$]-Exendin-4, [Asp(9)-H$_2$O]-Liraglutide, [Asp(16)-H$_2$O]-GLP-1(7-36), [Asp(9)-H$_2$O]-Glucagon, [Asp(15)-H$_2$O]-Glucagon, [Asp(21)-H$_2$O]-Glucagon, [Asn(28)-NH$_3$]-Glucagon, [Asp(9)-H$_2$O]-Oxyntomodulin, [Asp(15)-H$_2$O]-Oxyntomodulin, [Asp(21)-H$_2$O]-Oxyntomodulin, [Asn(28)-NH$_3$]-Oxyntomodulin, [Asn(32)-N H$_3$]-Oxyntomodulin, [Asn(34)-NH$_3$]-Oxyntomodulin, [Asn(35)-NH$_3$]-Oxyntomodulin and all peptides with the motif -Asn-X- and -Asp-X- which bind and activate both the glucagon and the GLP-1 receptor (Hjort et al., Journal of Biological Chemistry, 269, 30121-30124, 1994; Day J W et al., Nature Chem Biol, 5:749-757, 2009) and suppress body weight gain and reduce food intake which are described in patent applications WO 2008/071972, WO 2008/101017, WO 2009/155258, WO 2010/096052, WO 2010/096142, WO 2011/075393, WO 2008/152403, WO 2010/070251, WO 2010/070252, WO 2010/070253, WO 2010/070255, WO 2011/160630, WO 2011/006497, WO 2011/152181, WO 2011/152182, WO 2011/117415, WO 2011/117416, the contents of which are herein incorporated by reference, or GIP and peptides which bind and activate both the GIP and the GLP-1 receptor and optionally the glucagon receptor, and improve glycemic control, suppress body weight gain and reduce food intake as described in patent applications WO 2011/119657, WO 2012/138941, WO 2010/011439, WO 2010/148089, WO 2011/094337, and WO 2012/088116, the contents of which are herein incorporated by reference.

The peptide product of the invention may be used as a reference material, e.g. for the quality control of pharmaceutical peptides, particularly for use in a quality control method wherein the amount of undesired cyclic imide group containing by-products in a peptide product preparation is quantitatively determined.

Quantitative determination of by-products in a peptide product sample preferably involves mass spectrometry. In addition to mass spectrometry, the determination may involve a prior chromatographic procedure, e.g. in order to separate other impurities from the peptide product or from other ingredients of the composition. Preferably, mass spectrometry is combined with HPLC.

Mass spectrometry is based on a measurement of the mass-to-charge ratio of charged particles. In a typical mass spectrometry procedure, the sample is loaded onto the mass spectrometry instrument and volatilized. The sample components are ionized and the resulting ions are separated in the mass analyzer by electromagnetic fields. The resulting ions are detected and the signal is processed into a mass spectrum. For the ionization of peptide products, electrospray ionization (ESI) and matrix-assisted laser desorption/ionization (MALDI) may be used. The resulting ions may be detected by highly sensitive methods such as Orbitrap or Fourier Transform (FT)-Ion Cyclotron Resonance (ICR) detection systems.

By means of mass spectrometry, a peak derived from a cyclic imide group containing by-product may be identified, which differs from the mass of the non-cyclisized product by 18 (mass of H$_2$O) or 17 (mass of NH$_3$).

Further, the present invention shall be explained in more detail by the following examples describing synthesis, chromatographic purification and analytic characterization of the cyclic imide group containing peptide [Asp(9)-H$_2$O]-AVE0010.

EXAMPLES

1. Synthesis of [Asp(9)-H$_2$O]-AVE0010

[Asp(9)-H$_2$O]-AVE0010 is a by-product in the synthesis of the pharmaceutical peptide product AVE0010. It is generated when the side chain of amino acid Asp(9) forms an aspartimide with the N-atom of the adjacent amino acid Leu(10) under removal of water.

The amino acid sequence of [Asp(9)-H$_2$O]-AVE0010 is as follows:

H-His-Gly-Glu-Gly-Thr-Phe-Thr-Ser-X-Ser-Lys-Gln-

Met-Glu-Glu-Glu-Ala-Val-Arg-Leu-Phe-Ile-Glu-Trp-

Leu-Lys-Asn-Gly-Gly-Pro-Ser-Ser-Gly-Ala-Pro-Pro-

Ser-Lys-Lys-Lys-Lys-Lys-Lys-NH$_2$

Peptide synthesis was carried out with the peptide synthesizer Bio536 (CS Bio). As a starting material, N-terminally Fmoc protected (20-44)-AVE0010 resin was used. The starting material was prepared by peptide synthesis under standard conditions.

25.56 g Fmoc-(20-44)-AVE0010 resin were mixed with 250 ml DMF, stirred for 5 minutes and then swollen for 2 hours. DMF was then aspirated through a frit. After the swelling, Fmoc cleavage was carried out with 25% piperidine in DMF.

Then, amino acids Val(19) to Leu(10) were coupled to the starting material under standard conditions using amino acid derivatives with a Fmoc protected amino group and a protected side chain, e.g. an O-t-butyl (OtBu) protected Glu side chain, a trityl(Trt)-protected Gln side chain, a butyloxycarbonyl(Boc)-protected Lys side chain and a t-butyl(tBu)-protected Ser side chain.

Then, a Fmoc-Asp-OH building block (without side chain protection group) was coupled under conditions favouring the formation of an aspartimide group.

4.26 g Fmoc-Asp-OH, 1.9 g HOBT hydrate and 2 mL DIC in 250 mL DMF were mixed with the resin. The reaction mixture was stirred overnight. The coupling solution was then pumped out and the resin was washed twice with DMF. Then, 3 eq HOBT and 3 eq DIC in DMF were mixed with the resin. The resin was stirred over the weekend.

To determine the degree of aspartimide formation, a resin sample was treated with a cleavage mixture called King's Cocktail (D. S. King, C. G. Fields, G. B. Fields, Int. J. Peptide Protein Res. 36, 1990, 255-266) to liberate the aspartimide containing peptide from the resin. By means of mass-spectrometric measurements, it was found that the coupling product was mainly present in form of a cyclic aspartimide.

Subsequently, a solution of 2% of DBU in DMF was used for the Fmoc cleavage.

Finally, amino acids Ser(8) to Gly(1) were coupled under standard conditions except that the Fmoc protection group was not cleaved with piperidine but with DBU, in order to prevent an opening of the cyclic aspartimide group. As a result, 30.5 g [Asp(9)-H$_2$O]-AVE0010 on resin were obtained.

The cleavage of peptide from resin and the side chain protection group was carried out with King's Cocktail. 9.25 g raw product (purity of 23.4% as measured by UV at 215 nm) resulted from 30.5 g Fmoc protected resin after the solid phase synthesis.

The cleavage of the peptide from the resin was carried out under standard conditions (King et al., 1990, Supra). In total, 9.25 g of crude [Asp(9)-H$_2$O]-AVE0010 were obtained after drying under vacuum.

2. Chromatographic Purification of [Asp(9)-H$_2$O]-AVE0010

Purification was carried out by two RP-HPLC steps and subsequent freeze drying. The RP-HPLC steps were conducted with a Varian PrepStar device. Stainless steel columns packed with C18 reverse phase material (e.g. Daisogel C18 for the first step or Hydrospher C18 for the second step) were used as stationary phase. H$_2$O+0.1% trifluoroacetic acid were used as mobile phase A and acetonitrile as mobile phase B. The gradient was carried out at 0-80% mobile phase B (Daisogel) and 0-35% mobile phase B (Hydrospher), respectively.

Figure 3:
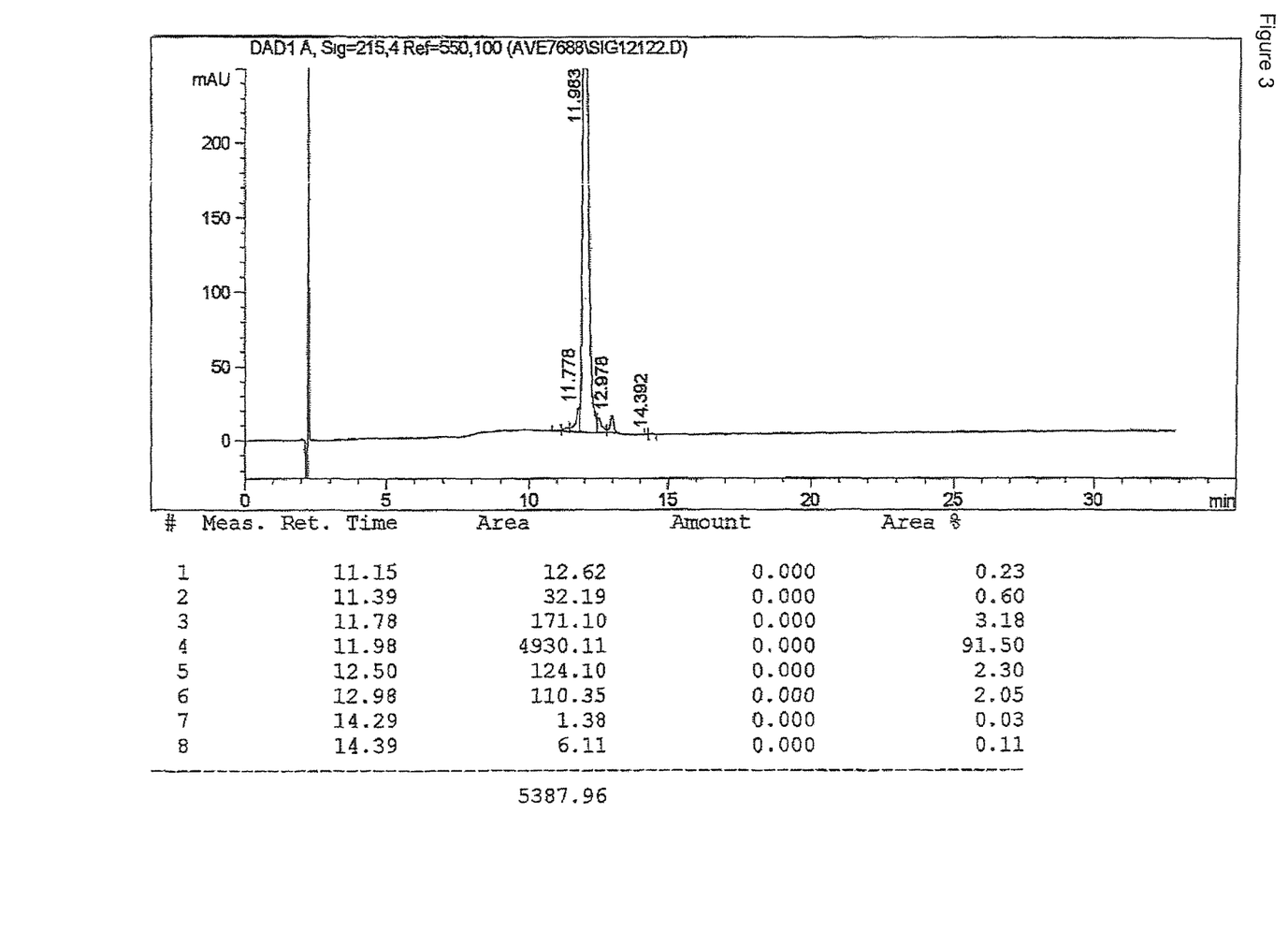
FIG. 3 is an analytical chromatogram of the purified product [ASQ(9)-H₂O]- AVE0010.

As a result, 540 mg [Asp(9)-H$_2$O]-AVE0010 with a purity of 91.50% (area ° as measured by HPLC) were obtained. An analytical chromatogram of the purified product is shown in FIG. 3.

3. Analytic Characterization

The purified product was characterized mass spectrometrically. Purified AVE0010 was used as a reference standard.

This analytic characterization showed the correct product [Asp(9)-H$_2$O]-AVE0010 with a molecular weight (M+H)$^+$ =4838.460, and the AVE0010 standard of 4856.544. The mass difference of [Asp(9)-H$_2$O]-AVE0010 to AVE0010 is 18.084 which equals to an H$_2$O molecule. The theoretical monoisotopic molecular weight of [Asp(9)-H$_2$O]-AVE0010 is 4837.534.

The invention claimed is:

1. A method of synthesizing a peptide product comprising at least one cyclic imide group of formula (I) or a salt or solvate thereof:

wherein
R$_1$ is a bridge of one or two atoms lengths,
R$_2$ is an amino acid side chain,
* denotes an asymmetric C atom, and
(*) denotes an optionally asymmetric C atom, comprising the steps:

(a) coupling a synthesis building block of formula (II):

(II)

wherein
X is a base-labile amino protecting group,
Y is an unprotected carboxy or carboxamido group,
* denotes an asymmetric C atom, and
Z is a carboxy group,
to a peptide product of formula (III)

(III)

wherein
$R_2$ is an optionally protected amino acid side chain,
$R_3$ is a peptidic residue bound to a solid phase carrier, and
(*) denotes an optionally asymmetric C atom under conditions wherein the cyclic imide group of formula (I) is formed,
(b) cleaving off the amino protecting group X,
(c) optionally continuing the peptide synthesis, and
(d) optionally purifying the peptide product (I).

2. The method of claim 1, wherein $R_1$ is —$CH_2$—.
3. The method of claim 1, wherein $R_1$ is —$CH_2$—$CH_2$—.
4. The method of claim 1, wherein Y is a carboxy group.
5. The method of claim 1, wherein Y is a carboxamido group.
6. The method of claim 1, wherein X is an Fmoc amino protecting group.
7. The method of claim 1, wherein the solid phase carrier is a resin.
8. The method of claim 1, wherein the coupling conditions in step (a) comprise a reaction time of at least 12 h, a temperature of between 15 and 40° C.
9. The method of claim 1, wherein the coupling conditions in step (a) comprise dimethylformamide (DMF) as organic solvent.
10. The method of claim 1, wherein the yield of a cyclic imide product in coupling step (a) is >50% based on the amount of the total yield of a coupling product in step (a).
11. The method of claim 1, wherein cleaving step (b) is carried out with a deprotecting agent selected from 1,8-diazabicyclo[5.4.0]undec-7-ene (DBU).
12. The method of claim 1, wherein the cyclic imide group of formula (I) is selectively introduced at least one predetermined position of the peptide product.
13. The method of claim 8, further comprising repeated addition of coupling reagents, wherein the coupling agents are selected from O-(benzotriazol-1-yl)-N,N,N',N'-tetramethyluronium tetrafluoroborate (TBTU), (2-(1H-benzotriazole-1-yl),1,1,3,3-tetramethyluronium) hexafluorophosphate (HBTU) with diisopropylethylamine (DIPEA), and 1-hydroxybenzotriazole/diisopropylcarbodiimide (HOBt/DIC).
14. The method of claim 1, wherein the least one cyclic imide group of formula (I) is at position Asp(9) of the peptide product.
15. The method of claim 1, wherein the peptide product comprising at least one cyclic imide group of formula (I) is lixisenatide having at least one cyclic imide group at position Asp(9).
16. The method of claim 1, wherein the peptide product comprising at least one cyclic imide group of formula (I) is selected from [Asp(9)-$H_2O$]-lixisenatide, [Asp(9)-$H_2O$]-exendin-4, [Asp(9)-$H_2O$]-liraglutide, and a salt or solvate thereof.
17. The method of claim 1, wherein the least one cyclic imide group of formula (I) is at position Asp(9), Asp(16), Asp(15), Asp(21), Asn(32), or Asn(35) of the peptide product.
18. The method of claim 1, wherein the peptide product comprising at least one cyclic imide group of formula (I) is selected from [Asp(9)-$H_2O$]-lixisenatide, [Asp(9)-$H_2O$]-exendin-4, [Asp(9)-$H_2O$]-liraglutide, [Asp(16)-$H_2O$]-GLP-1 (7-36), [Asp(9)-$H_2O$]-glucagon, [Asp(15)-$H_2O$]-glucagon, [Asp(21)-$H_2O$]-glucagon, [Asp(9)-$H_2O$]-oxyntomodulin, [Asp(15)-$H_2O$]-oxyntomodulin, [Asp(21)-$H_2O$]-oxyntomodulin, [Asn(32)-$NH_3$]-oxyntomodulin, [Asn(34)-$NH_3$]-oxyntomodulin, [Asn(35)-$NH_3$]-oxyntomodulin, and a salt or solvate thereof.

* * * * *

UNITED STATES PATENT AND TRADEMARK OFFICE
CERTIFICATE OF CORRECTION

| | |
|---|---|
| PATENT NO. | : 10,450,343 B2 |
| APPLICATION NO. | : 14/778502 |
| DATED | : October 22, 2019 |
| INVENTOR(S) | : Henkel |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 343 days.

Signed and Sealed this
Tenth Day of January, 2023

Katherine Kelly Vidal
*Director of the United States Patent and Trademark Office*